United States Patent [19]

Boese

[11] Patent Number: 4,678,340

[45] Date of Patent: Jul. 7, 1987

[54] SAMPLE HOLDER FOR POWDER X-RAY DIFFRACTOMETER

[75] Inventor: Roland Boese, Essen, Fed. Rep. of Germany

[73] Assignee: Nicolet Instrument Corporation, Madison, Wis.

[21] Appl. No.: 794,964

[22] Filed: Nov. 4, 1985

Related U.S. Application Data

[63] Continuation of Ser. No. 655,330, Sep. 27, 1984, abandoned.

[51] Int. Cl.[4] .............................................. B01F 11/02
[52] U.S. Cl. ................................... 366/111; 366/114; 366/127; 366/144
[58] Field of Search ...................... 366/108, 110–112, 366/114, 115, 127; 73/601, 606, 596; 134/184; 310/317, 316, 334–336

[56] References Cited

U.S. PATENT DOCUMENTS 3,405,916  10/1968  Carmichael ...................... 366/127 X
3,861,199   1/1975  Barkhoudarian ................. 73/67.5 R

FOREIGN PATENT DOCUMENTS 1598413  4/1970  Fed. Rep. of Germany .
2217157 12/1973  Fed. Rep. of Germany .

OTHER PUBLICATIONS

*NHK Laboratories Note*, Jul. 1979, pp. 2–13, Isao Fujimoto: "Dynamical Structure Analysis of LiNbO3 and LiTaO3 by Modulation X-ray Diffraction".
*Revue de Physique Appliquee*, Mar. 1973, p. 99, L. Trut, et al.: "Sur Un Dispositif Simple Destine A La Diffractometrie X De Poudre A Basse Temperature".

*Primary Examiner*—Timothy F. Simone
*Attorney, Agent, or Firm*—Kinney & Lange

[57] ABSTRACT

A sample holder to influence the texture and size of particles of a sample and/or to induce crystallization process in cooled liquids or gases. The vibrational energy of an ultrasonic radiator is transferred to the sample. In this manner, identification of samples by powder diffractometry are easier, quantitative determinations are more precise, and diffractometry of samples with a melting point below room temperature are possible.

11 Claims, 2 Drawing Figures

SAMPLE HOLDER FOR POWDER X-RAY DIFFRACTOMETER

This application is a continuation of Ser. No. 655,330, filed Sept. 27, 1984, now abandoned.

BACKGROUND OF THE INVENTION

1. Field of the Invention

The present invention relates to a sample holder for an x-ray powder diffractometer which uses an ultrasonic radiator either to reduce the texture effects of the sample or to induce a crystallization process from glasses or crystal obtained by the freezing of liquids or gases.

X-ray powder diffraction is an important technique for the qualitative and quantitative analysis of polycrystalline materials. The device described here is intended to extend the applicability of the x-ray powder diffraction method to classes of materials which are not normally analyzed by this technique and to improve the quality of x-ray powder diffraction data for other classes of materials for which texture effects present problems.

2. Description of the Prior Art

The conventional method for preparing specimens for analysis by x-ray powder diffraction normally involves the grinding of the sample to produce crystallites of small and equal size in random orientations. The successful application of the x-ray powder diffraction method for the identification and quantitative analysis of materials requires a statistical distribution of crystallite orientations to produce a diffraction pattern which is reproducible. For many types of specimens, it is difficult, time-consuming, and often impossible to obtain samples which exhibit statistically distributed crystallite orientations through the grinding process alone. The effects of non-statistical orientations which result from texture effects may be reduced to some extent by rotating the sample in a plane. However, rotating sample holders generally reduce texture effects in only one plane.

SUMMARY OF THE INVENTION

The present invention eliminates texture effects in all directions through the application of an ultrasonic vibrational frequency to the sample at the time of data collection. A second application for a sample holder with an ultrasonic radiator is in conjunction with low temperature techniques in powder diffraction. To date, the principal applications of low temperature methods to x-ray powder diffraction have been for the study of phase transitions or for the reduction of thermal vibrations in atoms as a means of sharpening the diffraction patterns. Most attempts to solidify gases or liquids directly on the sample holder have been unsuccessful because these materials tend to yield glasses or crystals which are too large. The sample holder described here eliminates these problems by inducing crystallization from glasses, randomizing crystallite orientations, and eliminating crystal size effects.

The objectives of this invention are to produce a statistical distributed orientation of crystallites, at the sample holder of a powder diffractometer, to produce reproducible particle sizes, and to induce crystallization from glassy solidified samples. These objectives are attained by attaching an ultrasonic generator to the sample holder of a powder diffractometer in such a way that the vibrational energy is transmitted directly to the specimen in the sample holder. In order to induce crystallization from a glass, the sample is simultaneously cooled with a low temperature device. Such a low temperature device is disclosed in co-pending application Ser. No. 646,561 filed Aug. 30, 1984 by the present inventor which is co-owned with the present invention and which is hereby incorporated by reference.

The achievable benefits of this invention consist specifically of providing a reproducible influence on the size of particles and texture of samples as a means of improving the qualitative and quantitative analysis of the sample under study. Inducing a crystallization process from glasses or crushing oversized crystals make it possible in conjunction with a low temperature device to produce powder diffraction patterns from samples which are liquids or gases at ambient conditions. This is possible in a quasi-continuous mode by pumping a gas or liquid through the sample holder then cooling it below its melting point while the sample holder is vibrated by the ultrasonic radiator. Thus, a process and monitoring is possible.

DETAILED DESCRIPTION OF THE PREFERRED EMBODIMENTS

Figure 1:
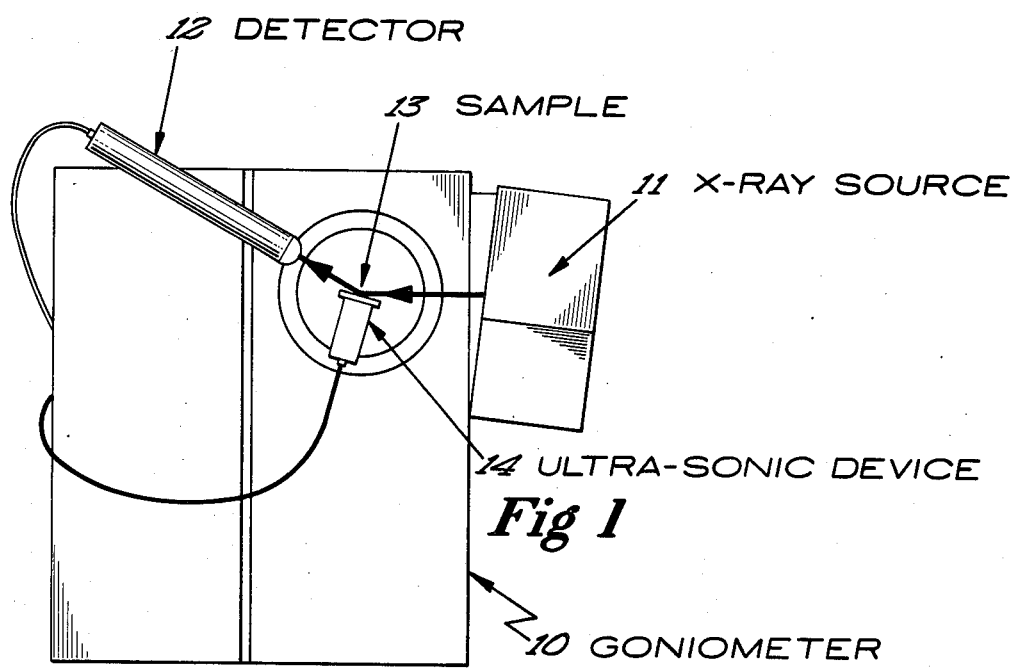
FIG. 1 illustrates the ultrasonic sample holder of the present invention within a diffractometer.

FIG. 1 illustrates a diffractometer in accordance with the present invention, including a goniometer designated generally at 10, an x-ray source 11, and a detector 12. A sample is positioned at a location 13 by an ultrasonic sample holding device 14.

Figure 2:
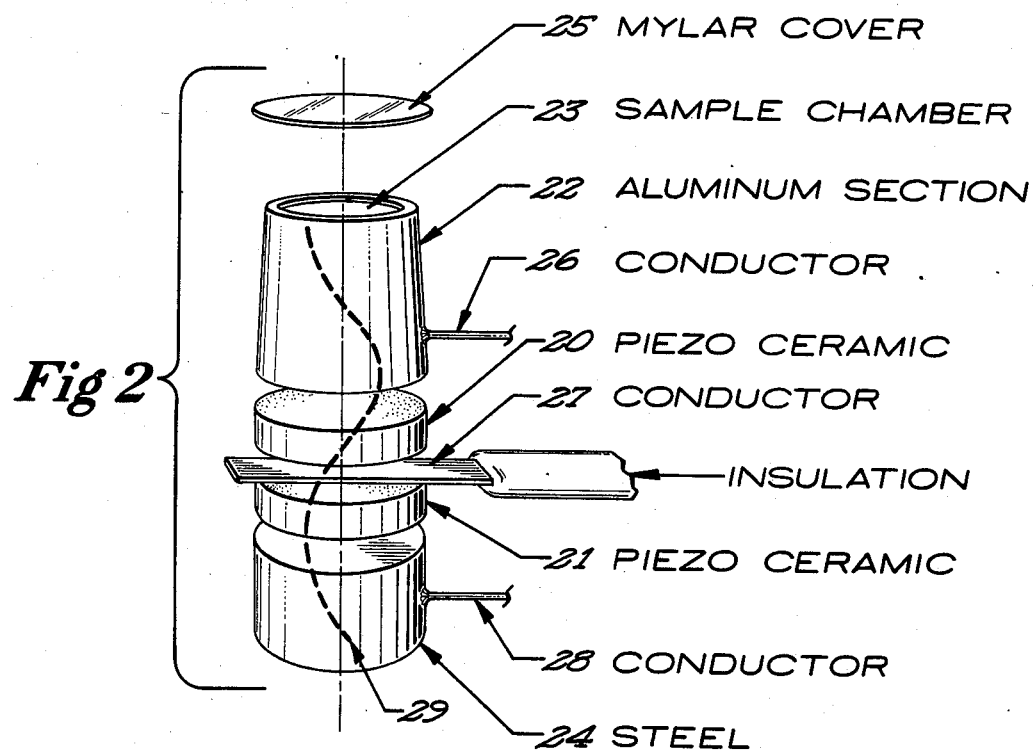
FIG. 2 is an exploded view of the sample holder of FIG. 1.

A preferred embodiment of the sample holder of the present invention is shown in FIG. 2 as a multi-sectioned device including two piezoceramic sections 20 and 21, an aluminum section 22 with a small depression to hold the sample 23, and a steel section 24. Conductors 26-28 connect the elements 22, 20 and 21, and 24 to a source of electrical energy. The use of aluminum as the sample holding section and steel as the bottom section increases the amplitude of vibration. The two piezoceramic sections 20 and 21 translate the electrical energy applied to the device, in known manner, into vibration energy to cause oscillation of the sample contained in the depression of the aluminum sample holding section of the device. Ultrasonic vibration of the sample is the objective of the present invention. A mylar cover 25 serves to hold the sample in place in the chamber 23.

In a manner known to those skilled in the art, cooling the device, or a sample contained therein, makes the device useful for producing glasses or crystals from substances that are liquid or gases at ambient conditions, and inducing crystallization therein.

The ultrasonic generator, when applied as described: (1) induces crystallization from glasses; (2) provides a self-grinding mechanism to reduce the size of large crystals; and (3) provides a random orientation of the crystals produced.

In the preferred embodiment, the ultrasonic generator produces a stationary wave represented by dotted line 29 which avoids increasing temperatures in the device by interference.

Obviously, many modifications and variations of the present invention are possible in light of the above teachings. It is therefore to be understood that the invention may be practiced otherwise than as specifically described.

What is claimed is:

1. An x-ray powder diffractometer comprising:
x-ray source means;
x-ray detector means; and
sample holder means for positioning a sample to be analyzed intermediate said source means and detector means, said sample holder means comprising sample chamber means for accepting a sample to be analyzed and ultrasonic generator means operatively connected to said sample chamber means for inducing ultrasonic vibration within a sample within said sample chamber means.

2. The x-ray powder diffractometer of claim 1 wherein said ultrasonic generator means comprises a first section formed of aluminum, the first section including a depression defining said sample chamber means, a second section formed of steel and piezo ceramic means intermediate said first and second sections.

3. The x-ray powder diffractometer of claim 2 wherein said ultrasonic generator is configured to produce a stationary wave.

4. The x-ray powder diffractometer of claim 1 wherein said ultrasonic generator is configured to produce a stationary wave.

5. The x-ray powder diffractometer of claim 1 wherein said ultrasonic generator means comprises means for producing glasses or crystals from substances that are liquid or gases at ambient conditions when used in conjunction with suitable cooling means.

6. The x-ray powder diffractometer of claim 5 wherein said ultrasonic generator means comprises means for providing self grinding of large crystals within said sample.

7. The x-ray powder diffractometer of claim 6 wherein said ultrasonic means comprises means for providing a random orientation of the crystals within said sample.

8. The x-ray powder diffractometer of claim 1 wherein said ultrasonic generator means comprises means for providing self grinding of large crystals within said sample.

9. The x-ray powder diffractometer of claim 1 wherein said ultrasonic means comprises means for providing a random orientation of the crystals within said sample.

10. The x-ray powder diffractometer of claim 1 wherein said ultrasonic means comprises means for eliminating texture effects within said sample.

11. In an x-ray powder diffractometer of the type having x-ray source means, having x-ray detector means and having sample holder means for positioning a sample to be analyzed intermediate said source means and detector means, the improvement wherein said sample holder means comprises sample chamber means for containing a sample to be analyzed and ultrasonic generator means operatively connected to said sample chamber means for inducing ultrasonic vibration of a sample contained within said sample chamber means.

* * * * *